(12) United States Patent
Itoh

(10) Patent No.: US 7,435,387 B2
(45) Date of Patent: Oct. 14, 2008

(54) TEST TUBE CAP REMOVING APPARATUS

(76) Inventor: Teruaki Itoh, 5-25, Kokaihommachi, Kumamoto-shi, Kumamoto-ken (JP)

( * ) Notice: Subject to any disclaimer, the term of this patent is extended or adjusted under 35 U.S.C. 154(b) by 584 days.

(21) Appl. No.: 10/923,821

(22) Filed: Aug. 24, 2004

(65) Prior Publication Data

US 2005/0047966 A1    Mar. 3, 2005

(30) Foreign Application Priority Data

Aug. 29, 2003    (JP)    ............... 2003-306492

(51) Int. Cl.
  *B01L 3/00*    (2006.01)
(52) U.S. Cl. ............... 422/99; 422/62; 422/63
(58) Field of Classification Search ............... 422/99; 53/246; 81/3.2, 3.36, 3.37, 3.39, 3.44, 90.1, 81/91.1, 128

See application file for complete search history.

(56) References Cited

U.S. PATENT DOCUMENTS 4,982,553 A * 1/1991 Itoh ............... 53/246

6,257,091 B1 * 7/2001 Cohen et al. ............... 81/3.2

FOREIGN PATENT DOCUMENTS

| JP | 54-162075 | 5/1978 |
|---|---|---|
| JP | 5-221488 | 8/1993 |
| JP | 5-228379 | 9/1993 |
| JP | 8-58890 | 3/1996 |
| JP | 8-91487 | 4/1996 |
| JP | 10-68734 | 3/1998 |
| JP | 2000-338111 | 12/2000 |
| JP | 2001-105118 | 4/2001 |

* cited by examiner

*Primary Examiner*—Walter D. Griffin
*Assistant Examiner*—Bobby Ramdhanie
(74) *Attorney, Agent, or Firm*—Nixon & Vanderhye P.C.

(57) ABSTRACT

A test tube cap removing apparatus includes a fixing unit that holds a test tube having an opening portion that is closed by a cap. A hold unit is situated above the cap in an axial direction of the test tube, has a position that is variable relative to the test tube in the axial direction, and is capable of contacting a top portion of the cap. A clamp unit is provided on the hold unit, supports the cap at side surfaces of the cap in a case where the hold unit is put in contact with the top portion of the cap, and removes the cap from the test tube in a case where the hold unit moves upwards relative to the test tube in the axial direction.

3 Claims, 5 Drawing Sheets

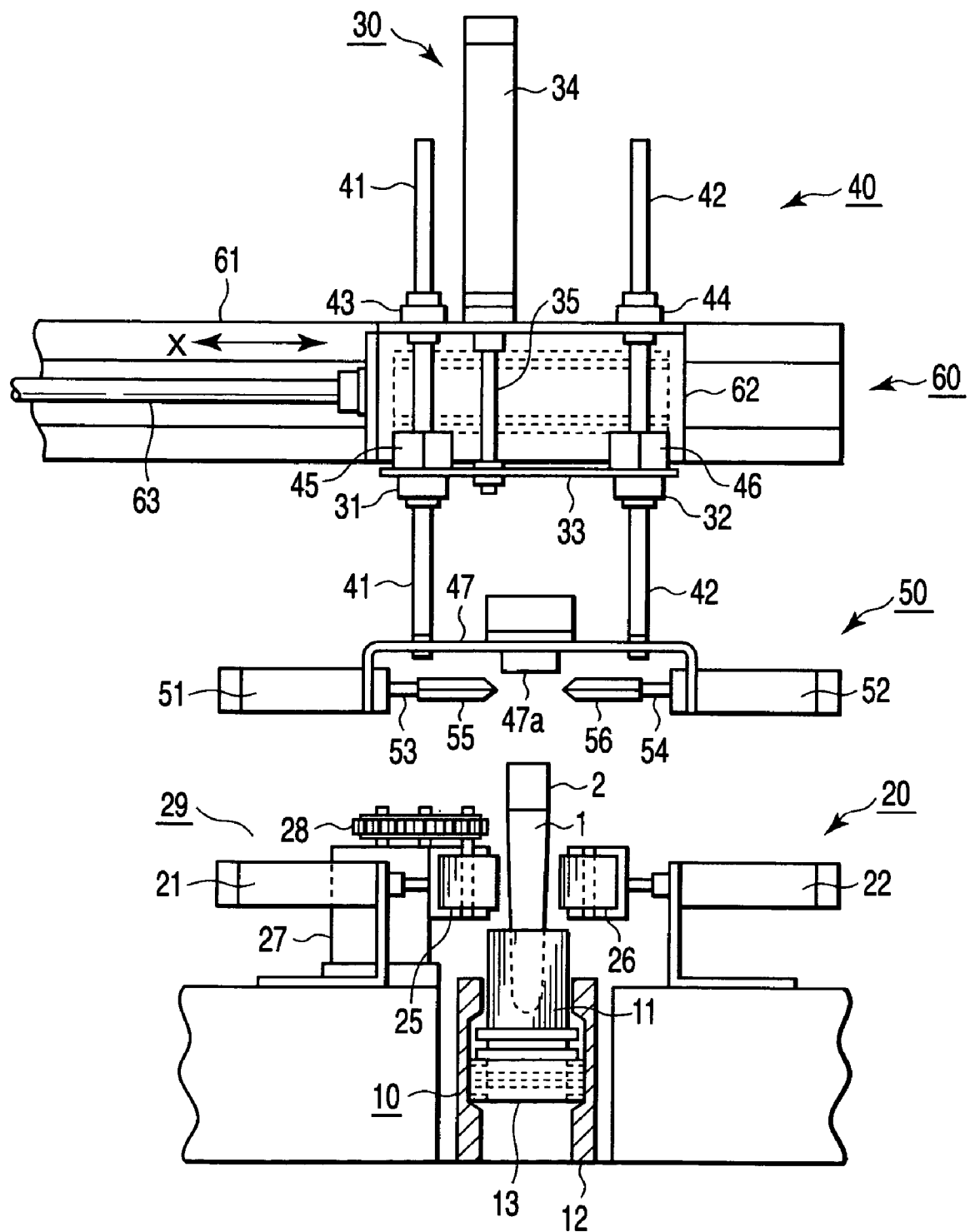
F I G. 1

TEST TUBE CAP REMOVING APPARATUS

CROSS-REFERENCE TO RELATED APPLICATIONS

This application is based upon and claims the benefit of priority from prior Japanese Patent Application No. 2003-306492, filed Aug. 29, 2003, the entire contents of which are incorporated herein by reference.

BACKGROUND OF THE INVENTION

1. Field of the Invention

The present invention relates to a test tube cap removing apparatus for automatically removing a cap that is attached to an opening portion of a test tube in which a specimen is to be contained.

2. Description of the Related Art

In a conventional test tube cap removing apparatus, a cap that closes the opening of a test tube is clamped by distal end portions of cap-removing arms in the state in which the test tube is clamped by a test tube clamper. In this apparatus, the cap-removing arms are pulled up by a cap-removing-arm drive cylinder, thereby automatically removing the cap.

Document 1 (Jpn. Pat. Appln. KOKAI Publication No. 5-228379) discloses a test tube cap removing apparatus wherein grippers are provided on the distal end portions of cap-removing arms. When the cap-removing arms are pulled up by a drive cylinder, the cap is rotated about its axis in association with inclining guides.

Test tubes, which are specimen containers, come in various sizes. For example, the relationship of "diameter×length" of the tube may be: $\phi13$ mm×75 mm, $\phi13$ mm×100 mm, $\phi16$ mm×75 mm, or $\phi16$ mm×100 mm. A specimen, such as blood, is contained in the test tube.

There are various types of caps for closing openings of test tubes, which include, for instance, a push-in type rubber cap, a cork cap, a screw cap, and a cap of a Sarstedt tube.

The test tube cap removing apparatus according to Document 1 is applicable to a case where a cap of a standard type, which is applied to a test tube of a fixed size, is to be removed.

However, with the test tube cap removing apparatus of Document 1, if the size of the test tube or the type of the cap is changed, it is difficult to remove the test tube cap.

In Document 1, the cap-removing arms of the test tube cap removing apparatus are provided with a mechanism for rotating the cap about its axis in association with the inclining guides when the cap is to be removed.

This rotating mechanism, however, is a mechanism that is designed mainly to reduce the force which is needed to remove the cap. This mechanism does not function to stably remove, e.g. a screw cap by rotating the screw cap with a necessary amount of rotation.

In short, Document 1 is silent on an adjusting mechanism for making the cap removing apparatus usable even when the size of the test tube or the type of the cap is changed. Such an adjusting mechanism is, for example, a mechanism for adjusting the positional relationship between a test tube clamper and a cap-removing arm, or a mechanism for removing a screw cap.

BRIEF SUMMARY OF THE INVENTION

According to an aspect of the present invention, there is provided a test tube cap removing apparatus comprising: a fixing unit that holds a test tube having an opening portion that is closed by a cap; a hold unit that is situated above the cap in an axial direction of the test tube, has a position that is variable relative to the test tube in the axial direction, and is capable of contacting a top portion of the cap; and a clamp unit that is provided on the hold unit, supports the cap at side surfaces of the cap in a case where the hold unit is put in contact with the top portion of the cap, and removes the cap from the test tube in a case where the hold unit moves upwards relative to the test tube in the axial direction.

BRIEF DESCRIPTION OF THE SEVERAL VIEWS OF THE DRAWING

FIG. 1 is a front view of an example of a test tube cap removing apparatus according to an embodiment of the present invention;

DETAILED DESCRIPTION OF THE INVENTION

Figure 2:
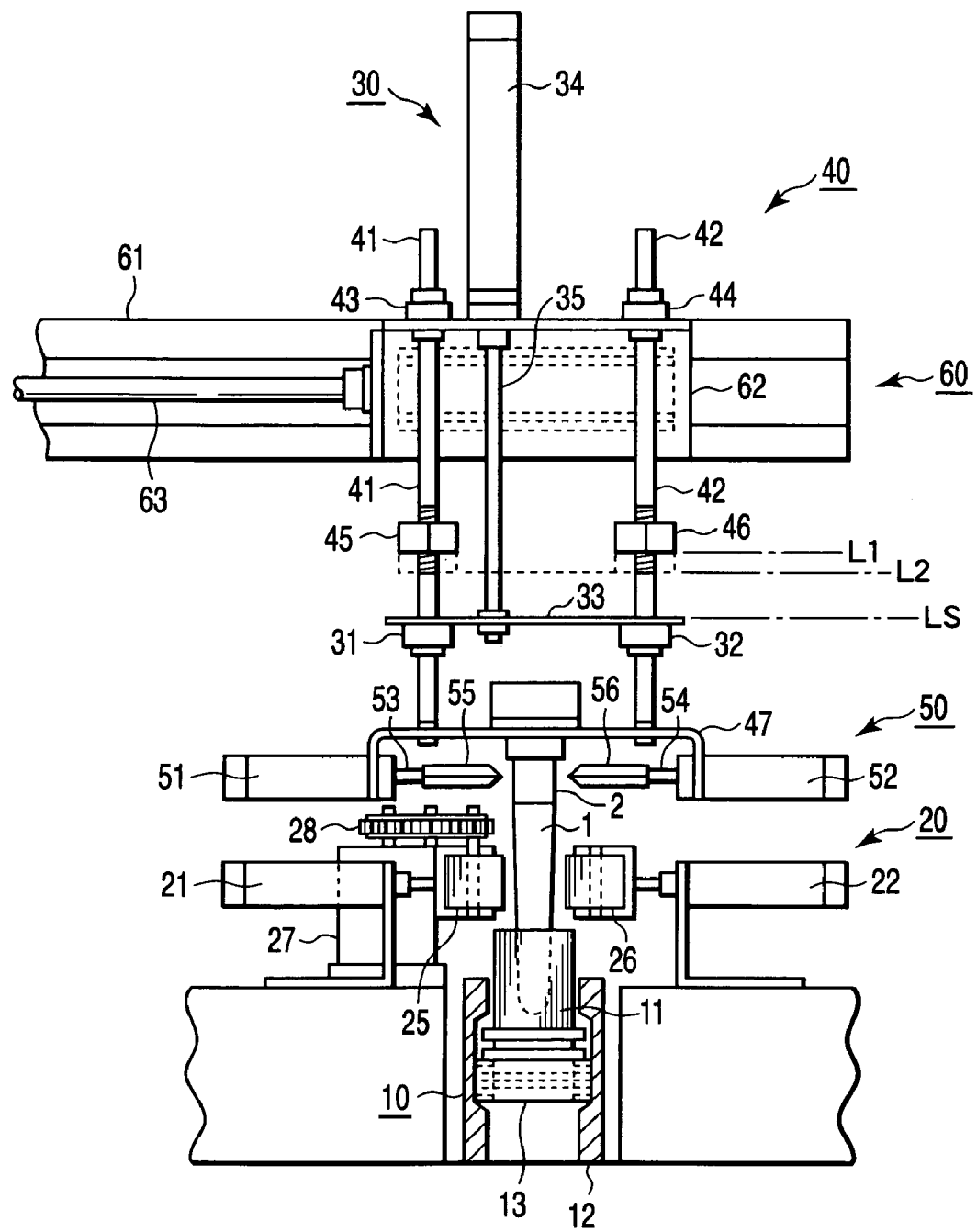
FIG. 2 is a front view of the example of the test tube cap removing apparatus in a state in which a drive unit reaches a lower limit position.

An embodiment of the present invention will now be described with reference to the accompanying drawings.

A test tube cap removing apparatus according to the embodiment, which is descried below, is capable of quickly and exactly removing a cap from a test tube even where test tubes of various sizes are used and various types of caps are attached to opening portions of test tubes.

FIG. 1 is a front view of an example of the test tube cap removing apparatus according to the embodiment of the present invention. FIG. 1 shows a first operation state of the apparatus.

A convey mechanism 10, which is provided below the test tube cap removing apparatus, conveys a test tube 1 with an opening closed by a cap 2, to a predetermined position where a cap removing operation is to be performed.

The convey mechanism 10 conveys a holder 11, which can hold the test tube 1 in a vertical state, to a predetermined position by means of a convey lane that comprises a guide rail 12 and a belt conveyor 13.

A fixing mechanism 20 clamps the test tube 1 from both sides, which has been conveyed to the predetermined position by the convey mechanism 10, and fixes the test tube 1.

The fixing mechanism 20 comprises a plurality of pressure-contact rollers 25, 26, piston/cylinder devices 21, 22, and a rotary drive mechanism 29.

The pressure-contact rollers 25 and 26 can clamp the test tube 1 from both sides. In this embodiment, two pressure-contact rollers 25 and 26 clamp the test tube 1. Alternatively, three or more pressure-contact rollers may clamp the test tube 1.

The piston/cylinder device 21, 22 advances/retreats the pressure-contact roller 25, 26, thereby putting the pressure-contact roller 25, 26 in pressure contact with the outer peripheral surface of the test tube 1 with a predetermined pressure, or separating the pressure-contact roller 25, 26 from the outer peripheral surface of the test tube 1.

The rotary drive mechanism 29 comprises a motor 27 and a deceleration mechanism 28.

The motor 27 rotates at least one of the pressure-contact rollers 25 and 26, thereby rotating the test tube 1 about its axis. In this embodiment, it is assumed that the motor 27 rotates the pressure-contact roller 25.

The deceleration mechanism 28 decelerates the rotation by the motor 27.

An elevation mechanism 30, which is provided above the fixing mechanism 20, vertically moves a drive unit, which is constructed by coupling slidable rings 31 and 32 using a coupling bar 33, by means of a piston/cylinder device 34.

A substantially middle part of the coupling bar 33 is connected to a driving end portion of a piston member 35 of the piston/cylinder device 34.

A hold mechanism 40 comprises a pair of elevation shafts 41 and 42, and a plate 47, which has both end portions coupled to lower end portions of the elevation shafts 41 and 42 and is horizontally suspended.

The hold mechanism 40 is coupled such that the hold mechanism 40 is vertically slidable in a predetermined range, relative to the drive unit, 31 to 33, of the elevation mechanism 30. A lower end portion of the hold mechanism 40 is provided with a plate 47 that is able to contact a top portion of the cap 2 of test tube 1 by its own weight.

The paired elevation shafts 41 and 42 are vertically movably supported on a pair of bearings 43 and 44 that are attached to a support frame 62 of a support mechanism 60. Nuts 45 and 46, which serve as stoppers, are engaged with the paired elevation shafts 41 and 42 at some points along their lengths. The vertical positions of the nuts 45 and 46 are adjustable so that the nuts 45 and 46 may be positioned at the same level.

The slidable rings 31 and 32 of the elevation mechanism 30 are slidably fitted on the paired elevation shafts 41 and 42 at positions below the positions where the nuts 45 and 46 are engaged.

A contact portion 47a, which comes in contact with the top portion of the cap 2 of test tube 1, is provided at a central part of the lower surface of the plate 47 that is attached to the lower end portions of the elevation shafts 41 and 42.

The contact portion 47a comes in contact with the top portion of the cap 2 of test tube 1 by its own weight. In this embodiment, the contact portion 47a is put in contact with the top portion of the cap 2 in the state in which the weight of the contact portion 47a, plate 47, elevation shafts 41 and 42, etc. acts on the top portion of the cap 2.

A clamp mechanism 50 is provided on the plate 47 of hold mechanism 40. When the plate 47 contacts the top portion of the cap 2, the clamp mechanism 50 clamps the cap 2 of test tube 1 from both sides.

In this embodiment, the clamp mechanism 50 comprises a pair of piston/cylinder devices 51 and 52, which are disposed at both ends of the plate 47 of hold mechanism 40, and clamp members 55 and 56, which are attached to piston members 53 and 54 of the paired piston/cylinder devices 51 and 52.

The clamp members 55 and 56 clamp the cap 2 of test tube 1 from both sides.

In this embodiment, in order to stably and surely clamp the cap 2, a distal end portion of each clamp member 55, 56 is formed to have a pointed shape.

In the support mechanism 60, the support frame 62, which has a rectangular plate shape, moves in the horizontal direction (direction X) along a supporting guide rail 61 that is horizontally situated. The support frame 62 is driven by a drive shaft 63 and is movable between a position above the test tube 1 and a position above a cap discard duct unit for discarding the cap 2.

In this embodiment, the test tube cap removing apparatus operates, for example, according to a sequence control of a central processing unit (CPU).

In the test tube cap removing apparatus according to the embodiment, the drive unit, 31 to 33, of the elevation mechanism 30 lowers the hold mechanism 40, brings the plate 47 into contact with the top portion of the cap 2, and stops the lowering of the hold mechanism 40.

As a result, the positions of the distal end portions of the clamp members 55 and 56 of the clamp mechanism 50, which is disposed on the plate 47, are set at such a level as to directly face lateral sides of the outer periphery of the cap 2.

Subsequently, only the drive unit, 31 to 33, of the elevation mechanism 30 continues to move downwards, and stops when the drive unit, 31 to 33, reaches a lower limit position of the movable range.

If the clamp mechanism 50 operates, the clamp members 55 and 56 clamp the cap 2. In the state in which the cap 2 is clamped by the clamp members 55 and 56, the drive unit, 31 to 33, of the elevation mechanisms 30 moves upwards.

Only the drive unit, 31 to 33, of the elevation mechanism 30 is first raised. When the drive unit, 31 to 33, abuts on the nuts 45 and 46 that serve as stoppers, the hold mechanism 40 is raised along with the drive unit, 31 to 33. As a result, the cap 2 is removed from the test tube 1.

In this embodiment, when the length size of the test tube varies, the level at which the plate 47 comes in contact with the top portion of the cap 2 will also vary in accordance with the variation in length of the test tube.

The test tube cap removing apparatus according to the present embodiment performs the same operation even if the length size of the test tube, which is to be set, is varied. Therefore, the test tube cap removing apparatus of this embodiment can properly remove the cap 2, without being affected by the length of the test tube 1.

In this embodiment, the clamp mechanism 50 includes the clamp members 55 and 56 with the pointed distal end portions that clamp the outer periphery of the cap 2. The cap 2 is clamped in the state in which the pointed distal end portions of the clamp members 55 and 56 bite the outer periphery of the cap 2. Thus, the cap 2 can stably and surely be clamped.

The fixing mechanism 20 of the test tube cap removing apparatus includes the rotary drive mechanism 29, which rotates at least one of the pressure-contact rollers 25 and 26 that clamp the test tube 1 from both sides with a predetermined pressure, thereby rotating the test tube 1 about its axis.

By the rotary drive mechanism 29, the test tube 1 can stably and continuously be rotated about its axis in a predetermined direction. As a result, even where the cap 2 attached to the test tube 1 is a screw cap, the cap 2 can stably and surely be removed.

Now referring to FIG. 1 to FIG. 5, the operation of the test tube cap removing apparatus will now be described.

As is shown in FIG. 1, the test tube 1 is conveyed to the predetermined position by the convey mechanism 10. The convey mechanism 10 has a stopping function. For example, the stopping function is realized in the following manner. A piston/cylinder device inserts a linear stopping pin, at a proper time, into a travel path along which the test tube holder 11 is conveyed over the convey lane. Thus, the test tube 1 is stopped at the predetermined position.

If the test tube 1 is stopped at the predetermined position, the test tube cap removing apparatus is set in a standby state for the cap removing operation.

The elevation mechanism 30 starts a lowering operation. With the lowering operation of the elevation mechanism 30, the drive unit, 31 to 33, move downwards. The hold mechanism 40, which is suspended by the drive unit, 31 to 33, also moves downwards. If the contact portion 47a of the plate 47 comes in contact with the top portion of the cap 2, the hold mechanism 40 stops lowering at this position. When the contact portion 47a of plate 47 is in contact with the cap 2, the weight of the plate 47, as well as the weight of the elevation shafts 41 and 42, etc., acts on the cap 2.

Thus, in the case where the length size of the test tube 1 is relatively large and the position of the top portion of the cap 2 is high, the level at which the plate 47 stops is high. On the other hand, in the case where the length size of the test tube 1 is relatively small and the position of the top portion of the cap 2 is low, the level at which the plate 47 stops is low.

Regardless of the position where the plate 47 stops, the positions of the distal end portions of the clamp members 55 and 56 of the clamp mechanism 50, which is disposed on the plate 47, are set at such a level as to substantially directly face lateral sides of the outer periphery of the cap 2.

Even after the lowering operation of the hold mechanism 40 is stopped, the elevation mechanism 30 continues the lowering operation.

The slidable rings 31 and 32 slide on the elevation shafts 41 and 42, and the drive unit, 31 to 33, continues the lowering operation. When the drive unit, 31 to 33, reaches a lower limit position of the movable range, the drive unit, 31 to 33, stops.

FIG. 2 is a front view of the example of the test tube cap removing apparatus in the state in which the drive unit, 31 to 33, reaches the lower limit position.

In FIG. 2, height levels L1, L2 and LS indicate various levels of the lowered drive unit, 31 to 33, of the elevation mechanism 30.

Level L1 indicates the level of the drive unit, 31 to 33, at the time when the contact portion 47a of the plate 47 comes in contact with the top portion of the cap 2 and the hold mechanism 40 stops lowering, in the case where the length size of the test tube 1 is relatively large and the level of the top portion of the cap 2 is high.

Level L2 indicates the level of the drive unit, 31 to 33, at the time when the contact portion 47a of the plate 47 comes in contact with the top portion of the cap 2 and the hold mechanism 40 stops lowering, in the case where the length size of the test tube 1 is relatively small and the level of the top portion of the cap 2 is low.

Level LS indicates the level of the drive unit, 31 to 33, in the case where the drive unit, 31 to 33, continues the lowering operation even after the stop of lowering of the hold mechanism 40, and finally the drive unit, 31 to 33, stops.

When the contact portion 47a of the plate 47 comes in contact with the top portion of the cap 2, the clamp mechanism 50 starts to operate. The clamp members 55 and 56 clamp the cap 2 from both sides.

Figure 3:
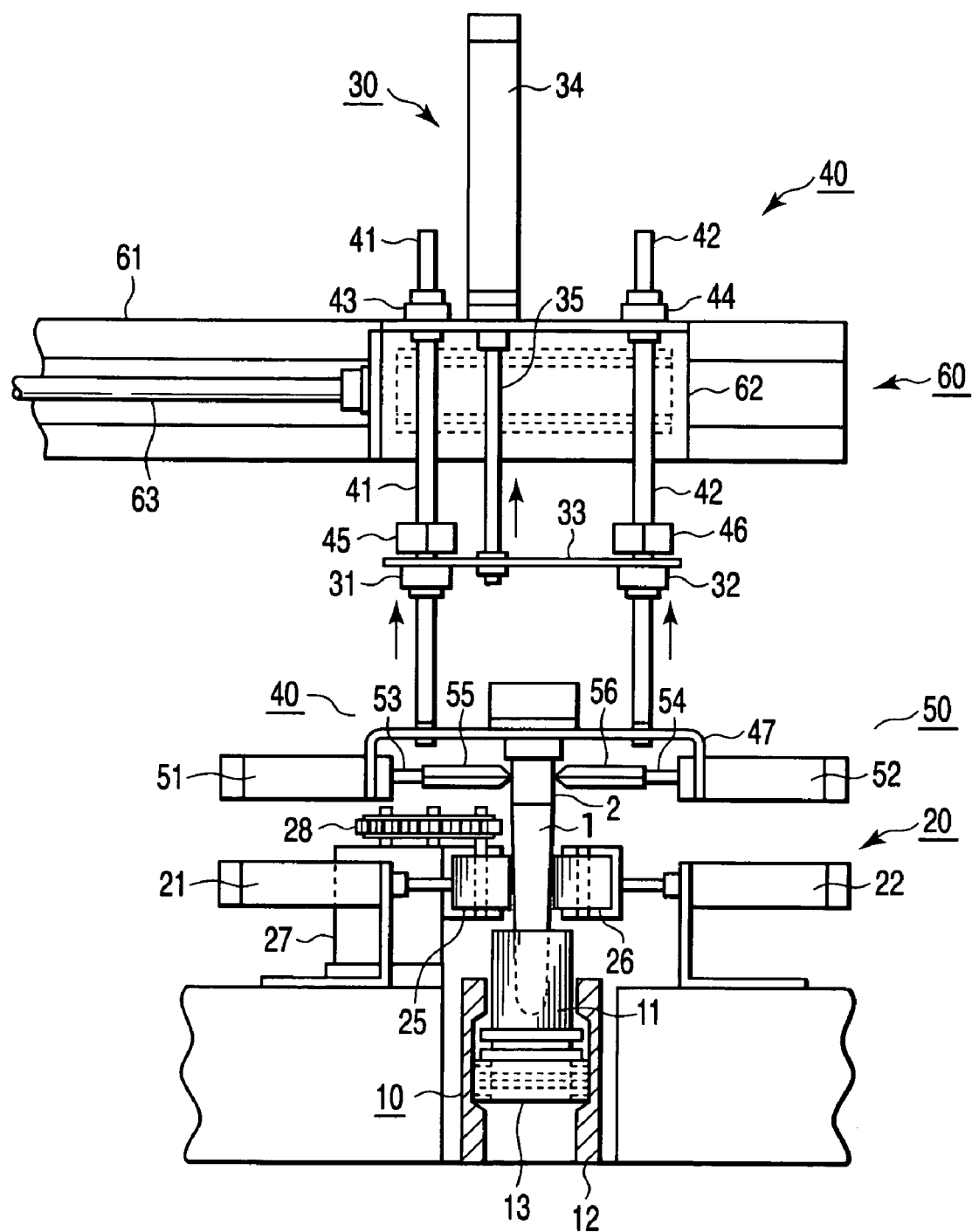
FIG. 3 is a front view of the example of the test tube cap removing apparatus at a time a cap removing operation is started.

FIG. 3 is a front view of the example of the test tube cap removing apparatus at a time the removing operation for removing the cap 2 is started.

In the state in which the cap 2 is clamped by the clamp members 55 and 56, the elevation mechanism 30 starts to operate. With the operation of the elevation mechanism 30, the drive unit, 31 to 33, starts to move upwards.

Only the drive unit, 31 to 33, moves upwards until the slidable rings 31 and 32 of the drive unit, 31 to 33, abut on the nuts 45 and 46 of the hold mechanism 40.

If the slidable rings 31 and 32 of the drive unit, 31 to 33, abut on the nuts 45 and 46 of the hold mechanism 40, the drive unit, 31 to 33, starts pulling up the hold mechanism 40.

Substantially at the same time as the hold mechanism 40 is pulled up, the motor 27 starts rotating in a predetermined direction.

With the rotation of the motor 27, the pressure-contact roller 25 rotates in a predetermined direction. Consequently, the test tube 1 is rotated in a predetermined direction by the rotation of the pressure-contact roller 25.

Figure 4:
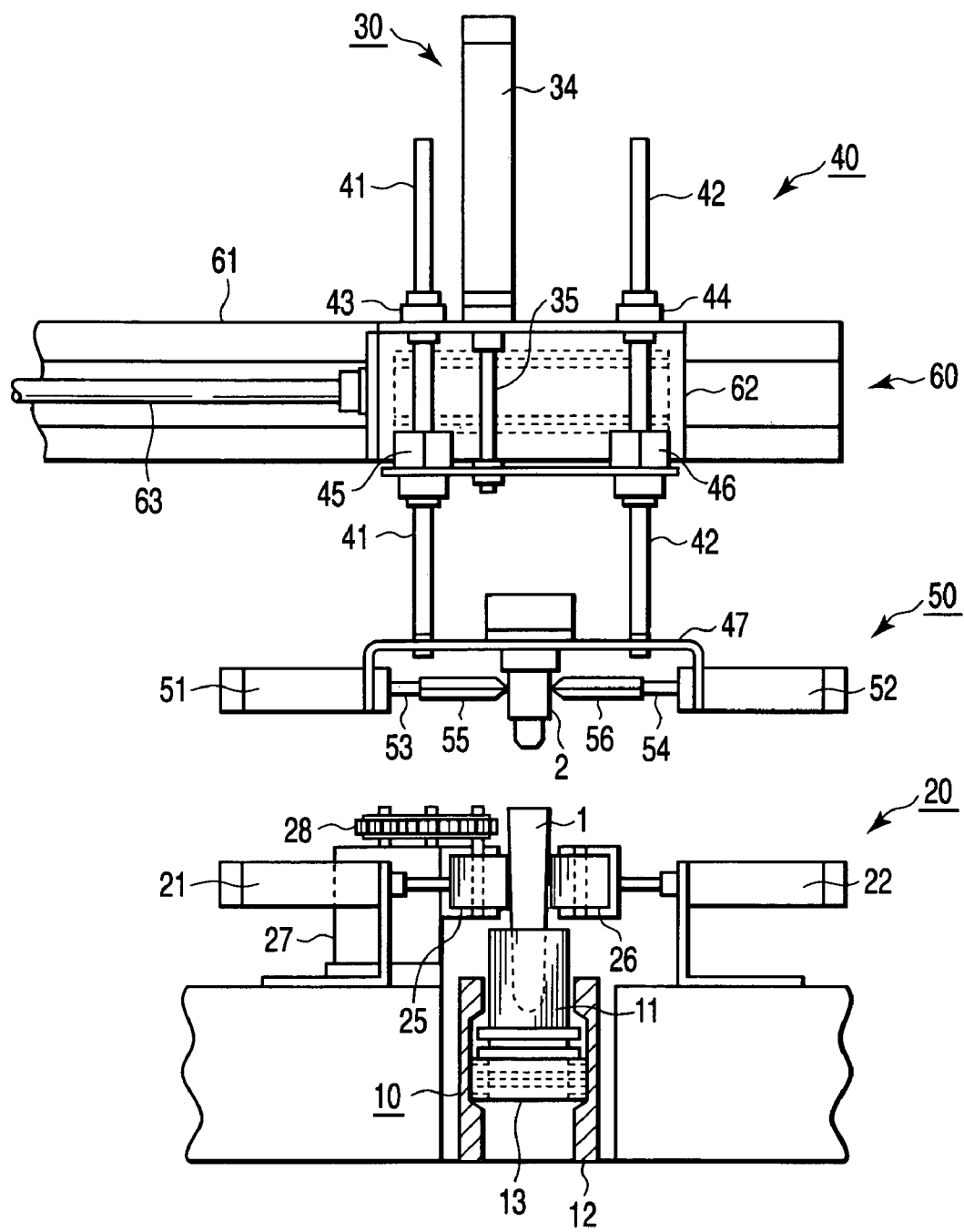
FIG. 4 is a front view of the example of the test tube cap removing apparatus at a time the cap removing operation is completed.

FIG. 4 is a front view of the example of the test tube cap removing apparatus at a time the removing operation for removing the cap 2 is completed.

With the pulling-up operation and the rotating operation combined, the operation for removing the cap 2 is smoothly started. The rotating operation is continuously performed for only a necessary time period by the rotary drive mechanism 29 that comprises the motor 27 and deceleration mechanism 28.

Thus, whether the cap 2 is a push-in type cap or a screw cap, it can be removed. With this test tube cap removing apparatus, any type of cap can be removed very stably.

Figure 5:
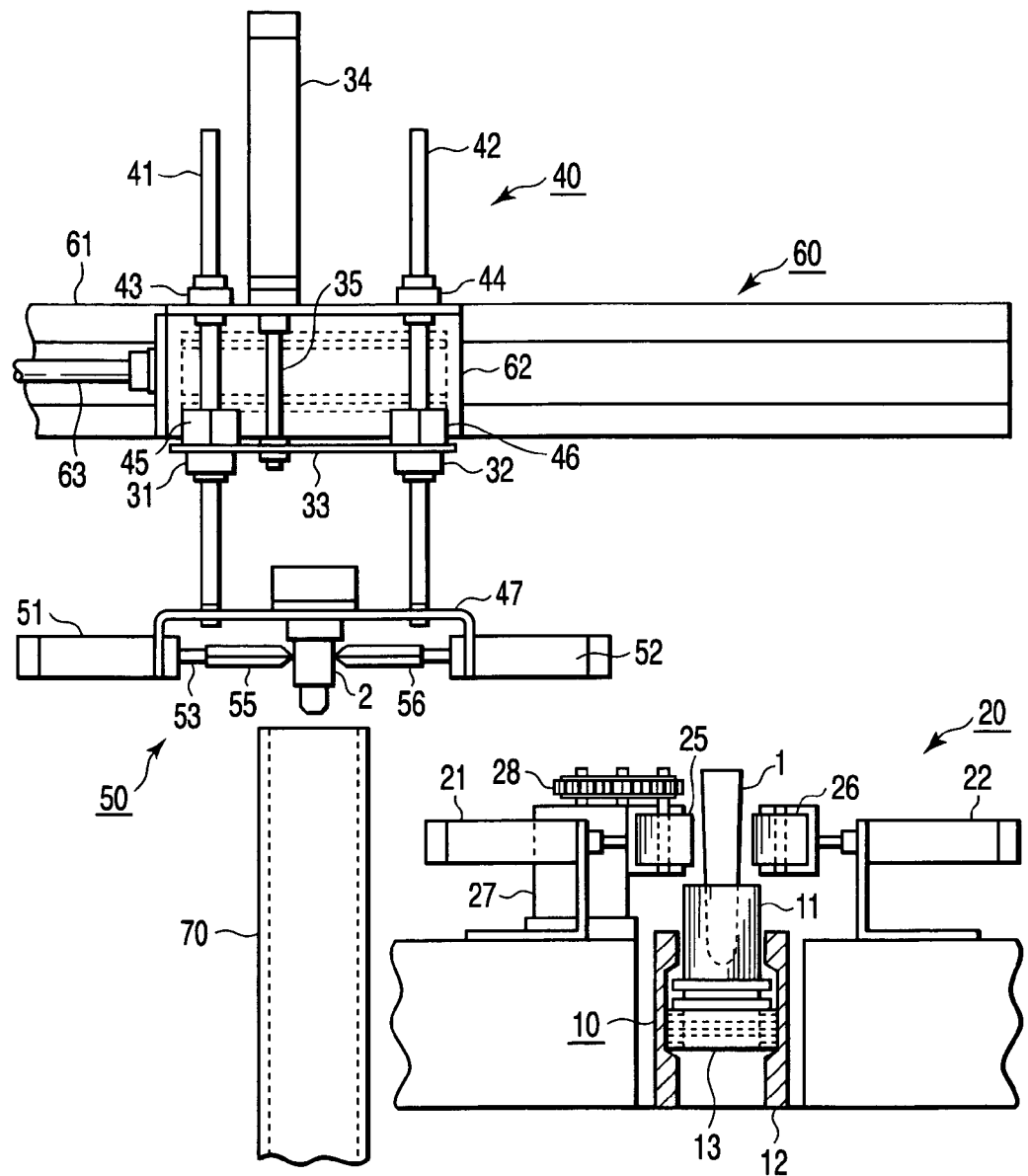
FIG. 5 is a front view of the example of the test tube cap removing apparatus in a state in which a clamp mechanism 50 is moved to a position above a cap discard duct.

FIG. 5 is a front view of the example of the test tube cap removing apparatus in the state in which the clamp mechanism 50 is moved to a position above a cap discard duct.

If the removal of the cap 2 is completed, the operation of the support mechanism 60 is started. With the operation of the support mechanism 60, the support frame 62 is pulled to the left (in FIG. 4) by the drive shaft 63 and is moved along the support guide rail 61 to a position above a cap discard duct 70.

In this state, the paired piston/cylinder devices 51 and 52, which are attached to the plate 47 of the hold mechanism 40, are rendered non-operative.

Since the paired piston/cylinder devices 51 and 52 are set in the non-operative state, the distal end portions of the clamp members 55 and 56 of clamp mechanism 50 are separated from the outer periphery of the cap 2. As a result, the cap 2 is discarded in the cap discard duct 70 so that the cap 2 may be disposed of.

FIG. 5 shows the state immediately before the cap 2 is discarded in the cap discard duct 70.

After the cap 2 is discarded, the support frame 62 moves back to a position above the convey mechanism 10 and fixing mechanism 20. The test tube cap removing apparatus is thus restored to the initial state. Subsequently, the similar operations are to be repeated.

In the above-described embodiment, when the plate 47 of hold mechanism 40 comes in contact with the top portion of the cap 2 by its own weight, the clamp mechanism 50 clamps the cap 2.

In addition, in the embodiment, the cap 2 is removed while the test tube 1 and cap 2 are rotated relative to each other.

Therefore, even where the size of the test tube varies, or even where the type of the cap varies, the cap can quickly and properly be removed from the test tube.

In this embodiment, test tubes 2, from which caps 2 are removed, may successively be fed to a specimen analysis apparatus.

In the present embodiment, the piston/cylinder device is used as a drive actuator. Alternatively, an electromagnetic actuator, for instance, may be used as a drive actuator.

In the embodiment, the axis of the test tube 1 is set to be vertical. Alternatively, the axis of the test tube 1 may be set at an angle to the vertical direction. In this case, the piston/cylinder devices 21, 22, 51 and 52 may be configured to operate in a direction perpendicular to the axis of the test tube 1. In addition, the elevation mechanism 30 and hold mechanism 40 may be configured to operate in the axial direction of the test tube 1.

What is claimed is:

1. A test tube cap removing apparatus comprising:
   a plate that is situated above a cap in an axial direction of a test tube having an opening portion that is closed by the cap, a position of the plate being variable relative to the test tube in the axial direction, the plate including a contact portion that is capable of contacting a top portion of the cap;
   a clamp unit that is provided on the plate, the clamp unit supporting the cap at side surfaces of the cap when the contact portion of the plate is put in contact with the top portion of the cap, and the clamp unit removing the cap from the test tube when the plate moves upwards relative to the test tube in the axial direction;
   elevation shafts that horizontally suspend the plate;
   slidable rings that are slidably fitted on the elevation shafts;
   a coupling bar that couples the slidable rings;
   a piston/cylinder device that is connected to the coupling bar, and that vertically moves a drive unit comprising the slidable rings and the coupling bar in the axial direction;
   a hold mechanism that comprises the elevation shafts and the plate and is vertically slidable;
   a plurality of rollers that directly clamp the test tube at side surfaces of the test tube with a predetermined pressure; and
   a rotary drive mechanism that rotates at least one of the rollers thereby rotating the test tube about an axis of the test tube,
   wherein the test tube cap removing apparatus performs a lowering operation of the drive unit and a lowering operation of the hold mechanism, stops the hold mechanism lowering when the contact portion of the plate comes in contact with the top portion of the cap, and continues the lowering operation of the drive unit, stops the lowering operation of the drive unit when the drive unit reaches a lower limit position, makes the clamp units clamp the cap, starts the drive unit to move upwards in the state in which the cap is clamped by the drive unit, and starts a pulling-up operation of both the drive unit and the hold mechanism while starting a rotating operation for the test tube by the rotary drive mechanism.

2. The test tube cap removing apparatus according to claim 1, wherein distal end portions of the clamp unit, which clamp the side surfaces of the cap, have pointed shapes.

3. A test tube cap removing apparatus comprising:
   a plate that is situated above a cap in an axial direction of a test tube having an opening portion that is closed by the cap, a position of the plate being variable relative to the test tube in the axial direction, the plate including a contact portion that is capable of contacting a top portion of the cap;
   a clamp unit that is provided on the plate, the clamp unit supporting the cap at side surfaces of the cap when the contact portion of the plate is put in contact with the top portion of the cap, and the clamp unit removing the cap from the test tube when the plate moves upwards relative to the test tube in the axial direction;
   elevation shafts that horizontally suspend the plate;
   slidable rings that are slidably fitted on the elevation shafts;
   a coupling bar that couples the slidable rings;
   a piston/cylinder device that is connected to the coupling bar, and that vertically moves a drive unit comprising the slidable rings and the coupling bar in the axial direction;
   a hold mechanism that comprises the elevation shafts and the plate and is vertically slidable;
   a plurality of rollers that directly clamp the test tube at side surfaces of the test tube with a predetermined pressure; and
   a rotary drive mechanism that rotates at least one of the rollers thereby rotating the test tube about an axis of the test tube,
   wherein the drive unit is axially displaceable between a raised position and a lower limit position, the drive unit being displaced from the raised position to the lower limit position regardless of a size of the test tube, and
   wherein the hold mechanism is axially displaceable between a top position and an engaged position, the engaged position and thus a displacement amount of the hold mechanism varying depending on the size of the test tube.

* * * * *